United States Patent
Riistaniemi et al.

(10) Patent No.: US 10,049,766 B1
(45) Date of Patent: Aug. 14, 2018

(54) METHOD AND APPARATUS FOR SECURE SETUP OF CLINICAL TRIAL CLIENT DEVICE

(71) Applicant: CRF Box Oy, Helsinki (FI)

(72) Inventors: Tony Riistaniemi, Helsinki (FI); Jani Veikkolainen, Järvenpää (FI)

(73) Assignee: CRF BOX OY, Helsinki (FI)

( * ) Notice: Subject to any disclaimer, the term of this patent is extended or adjusted under 35 U.S.C. 154(b) by 0 days.

(21) Appl. No.: 15/850,851

(22) Filed: Dec. 21, 2017

(30) Foreign Application Priority Data

Feb. 15, 2017 (FI) ...................................... 20175125

(51) Int. Cl.
| | |
|---|---|
| *H04L 29/06* | (2006.01) |
| *G16H 10/20* | (2018.01) |
| *G06F 7/04* | (2006.01) |
| *G06F 15/16* | (2006.01) |
| *G06F 17/30* | (2006.01) |
| *H04L 9/32* | (2006.01) |
| *G16H 10/60* | (2018.01) |

(52) U.S. Cl.
CPC .......... *G16H 10/20* (2018.01); *G16H 10/60* (2018.01); *H04L 9/32* (2013.01); *H04L 63/08* (2013.01)

(58) Field of Classification Search
None
See application file for complete search history.

(56) References Cited

U.S. PATENT DOCUMENTS

| | | | | |
|---|---|---|---|---|
| 7,421,697 | B2 * | 9/2008 | Takahashi | G06F 9/4418 715/750 |
| 2004/0078216 | A1 | 4/2004 | Toto | |
| 2004/0153675 | A1 * | 8/2004 | Dorn | G06F 21/31 726/5 |

(Continued)

FOREIGN PATENT DOCUMENTS

WO     2016132315 A1     8/2016

OTHER PUBLICATIONS

Finnish Patent and Registration Office Action, Application No. 20175125, dated May 22, 2017, 8 pages.

(Continued)

*Primary Examiner* — Eric Chen
(74) *Attorney, Agent, or Firm* — Ziegler IP Law Group, LLC

(57) ABSTRACT

A method, device and system for transceiving clinical trial related information includes a client device and a server that communicate. An application of the client device has a client application of a clinical trial service whose server application is running on the server. A coordinator user profile with credentials and a user profile with credentials are maintained. The coordinator credentials are determined to be be authorized. The coordinator user obtains access to the application. Coordinator input data triggers user change for the client device. A request to the server application indicating the triggered user change is sent. Credentials are received from the server application and associated with the user profile. The coordinator user is logged out by disconnecting coordinator level access to the proprietary application and resetting the coordinator credentials and session data within the client device. The credentials are stored for automatic first logging in of the user.

17 Claims, 3 Drawing Sheets

(56) References Cited

U.S. PATENT DOCUMENTS

| | | | | |
|---|---|---|---|---|
| 2005/0204146 | A1* | 9/2005 | Kebinger | G06F 21/31 |
| | | | | 713/182 |
| 2009/0313045 | A1* | 12/2009 | Boyce | G16H 10/20 |
| | | | | 705/3 |
| 2011/0225011 | A1 | 9/2011 | Keskiivari et al. | |
| 2012/0323796 | A1* | 12/2012 | Udani | G06Q 50/24 |
| | | | | 705/80 |
| 2013/0218594 | A1* | 8/2013 | Skocic | G06Q 10/10 |
| | | | | 705/3 |
| 2014/0222444 | A1 | 8/2014 | Cerello | |
| 2015/0039327 | A1 | 2/2015 | Pal | |
| 2015/0324550 | A1 | 11/2015 | Hurley | |
| 2016/0063131 | A1* | 3/2016 | Kuscher | H04L 67/02 |
| | | | | 715/234 |
| 2016/0063226 | A1* | 3/2016 | Singh | G06F 21/30 |
| | | | | 726/3 |

OTHER PUBLICATIONS

Finnish Patent and Registration Office, Office Action, Application No. 20175125, dated Sep. 8, 2017, 4 pages.
Extended European Search Report, Application No. 18156456.8-1126, dated May 17, 2018, 5 Pages.

\* cited by examiner

METHOD AND APPARATUS FOR SECURE SETUP OF CLINICAL TRIAL CLIENT DEVICE

TECHNICAL FIELD

The present application generally relates to clinical trials and securely setting up client devices for subject users of the clinical trial.

BACKGROUND

This section illustrates useful background information without admission of any technique described herein representative of the state of the art.

New medical innovations, such as new drugs, medical devices, or medical applications, are often researched and tested using clinical trials. Trials require more than one phase of testing that take several years and cost considerable amounts of money to perform.

Clinical trials are typically classified into 4 phases (unless trial is interrupted or closed). Clinical trials of drugs may not fit into a single phase. For example, some clinical trials may blend from phase I to phase II or from phase II to phase III. The drug-development process may normally proceed through all four phases over many years. If a drug successfully passes through phases I, II and III, the drug may be approved by a national regulatory authority for use in general population, for example. Phase IV may correspond to 'post-approval' studies.

Each phase has a different purpose and helps researchers answer different questions. In phase I trials, researchers test an experimental drug or treatment in a small group of people (20-80) for the first time. The purpose is to evaluate its safety and identify side effects. In phase II trials, the experimental drug or treatment is administered to a larger group of people (100-300) to test its efficacy or effectiveness and to further evaluate its safety. In phase III trials, the experimental drug or treatment is administered to larger groups of people (1,000-3,000) to confirm its effectiveness, monitor side effects, compare it with standard or equivalent treatments, and collect information that will allow the experimental drug or treatment to be used safely. In phase IV trials, after a drug is approved by a regulatory authority, such as Food and Drug Administration (FDA) in the USA, and made available to the public, researchers track its safety, seeking more information about a drug or treatment's risks, benefits, and optimal use.

Typically, a clinical trial or study is funded by a sponsor, such as a private company, medical or research institution, federal agency, or by an entity established by a collaboration of such groups. The sponsor may employ one or more clinical investigators or research assistants to oversee administration of and/or monitor the study at one or more investigation sites. Each investigation site may include a number of study participants.

When a participant in a clinical trial fills in an electronic diary or study, a client device is used. The device may be used by a plurality of subject users one after another, clinical trial after another.

Traditionally, when a site coordinator sets up the client device to be handed over to the subject user, username and password are delivered to the subject user by email or simply typed or printed on paper. The client device with an application being used for processing and/or transceiving data relating to a clinical trial is set up and provisioned by site personnel and handed over to a subject user. Resetting currently authenticated user session before authentication of the next subject user may needed to be done manually by the site personnel.

Thus, a solution is needed to enable more secure and efficient resetting of earlier session data and providing credentials for the subject user when providing a client device to be used in a clinical trial.

SUMMARY

Various aspects of examples of the disclosed embodiments are set out in the claims.

According to a first example aspect of the present disclosure, there is provided a computer implemented method for transceiving clinical trial related information between a client device operable by a plurality of users and a server apparatus, the client device and the server apparatus configured to communicate via a data network, a proprietary application of the client device comprising a client application of a clinical trial service whose server application is running on the server apparatus, wherein a coordinator user profile associated with coordinator credentials and a subject user profile associated with subject credentials are maintained by the server application at the server apparatus, the method comprising:

receiving the coordinator credentials via a user interface by the proprietary application, accepting the coordinator credentials in response to determining the coordinator credentials being authorized credentials, and logging in the coordinator user by providing coordinator level access to the proprietary application;

receiving, by the proprietary application, coordinator input data configured to trigger user change for the client device;

generating and sending, in response to the coordinator input data, a request by the proprietary application to the server application indicating the triggered user change;

receiving, by the proprietary application, subject credentials from the server application, wherein the subject credentials are associated with the subject user profile generated by the server application;

logging out the coordinator user by disconnecting coordinator level access to the proprietary application and resetting the coordinator credentials and session data within the client device; and storing the subject credentials by the proprietary application for automatic first logging in of the subject user.

In an embodiment, the request comprises an identifier for the subject user.

In an embodiment, the method further comprises:
logging in the subject user by providing subject level access to the proprietary application using the subject credentials.

In an embodiment, the method further comprises: prefilling by the proprietary application a login request template with the subject credentials.

In an embodiment, the method further comprises:
automatically sending a request by the proprietary application to the server application to login the subject user using the subject credentials.

In an embodiment, the method further comprises:
receiving subject user input data by the proprietary application; and
sending a request by the proprietary application to the server application to login the subject user in response to the received user input data.

In an embodiment, the subject user input data comprises at least one of the following:
  detected user input data via the user interface; and
  detected biometric data via a biometric sensor of the client device.

In an embodiment, the detected biometric data may comprise fingerprint data via a fingerprint sensor, iris recognition data via an iris scanner, voice recognition data via a voice recognition device, or face recognition data via a face recognition device of the client device, for example.

In an embodiment, the method further comprises:
  receiving activation data, by the proprietary application, from a sensing device of the client device, the sensing device comprising a positioning or a movement sensor; and
  sending a request by the proprietary application to the server application to login the subject user in response to the received activation data configured to indicate the client device being taken into use by the subject user.

According to a second example aspect of the present disclosure, there is provided a client device for transceiving clinical trial related information between the client device operable by a plurality of users and a server apparatus, the client device and the server apparatus configured to communicate via a data network, a proprietary application of the client device comprising a client application of a clinical trial service whose server application is running on the server apparatus, wherein a coordinator user profile associated with coordinator credentials and a subject user profile associated with subject credentials are maintained by the server application at the server apparatus, the client device comprising:
  a communication interface for transceiving information over a network;
  at least one memory including computer program code; the at least one memory and the computer program code configured to, with the at least one processor, cause the client device to:
    receive, by the proprietary application, the coordinator credentials via a user interface, accepting the coordinator credentials in response to determining the coordinator credentials being authorized credentials, and logging in the coordinator user by providing coordinator level access to the proprietary application;
    receive coordinator input data by the proprietary application configured to trigger user change for the client device;
    generate and send, in response to the coordinator input data, a request by the proprietary application to the server application indicating the triggered user change;
    receive, by the proprietary application, subject credentials from the server application, wherein the subject credentials are associated with the subject user profile generated by the server application;
    log out the coordinator user by disconnecting coordinator level access to the proprietary application and resetting the coordinator credentials and session data within the client device; and
    store the subject credentials by the proprietary application for automatic first logging in of the subject user.

According to a third example aspect of the present disclosure, there is provided a computer program embodied on a computer readable non-transitory medium for transceiving clinical trial related information between a client device operable by a plurality of users and a server apparatus, the client device and the server apparatus configured to communicate via a data network, a proprietary application of the client device comprising a client application of a clinical trial service whose server application is running on the server apparatus, wherein a coordinator user profile associated with coordinator credentials and a subject user profile associated with subject credentials are maintained by the server application at the server apparatus, the computer program comprising computer executable program code, which when executed by at least one processor of the client device, causes the client device to:
  receive the coordinator credentials via a user interface by the proprietary application, accepting the coordinator credentials in response to determining the coordinator credentials being authorized credentials, and logging in the coordinator user by providing coordinator level access to the proprietary application;
  receive, by the proprietary application, coordinator input data configured to trigger user change for the client device;
  generate and send, in response to the coordinator input data, a request by the proprietary application to the server application indicating the triggered user change;
  receive, by the proprietary application, subject credentials from the server application, wherein the subject credentials are associated with the subject user profile generated by the server application;
  log out the coordinator user by disconnecting coordinator level access to the proprietary application and resetting the coordinator credentials and session data within the client device; and
  store the subject credentials by the proprietary application for automatic first logging in of the subject user.

Different non-binding example aspects and embodiments of the present disclosure have been illustrated in the foregoing. The embodiments in the foregoing are used merely to explain selected aspects or steps that may be utilized in implementations of the present invention. Some embodiments may be presented only with reference to certain example aspects of the invention. It should be appreciated that corresponding embodiments may apply to other example aspects as well.

BRIEF DESCRIPTION OF THE DRAWINGS

For a more complete understanding of example embodiments of the present disclosure, reference is now made to the following descriptions taken in connection with the accompanying drawings in which.

DETAILED DESCRIPTION OF THE DRAWINGS

An example embodiment of the present disclosure and its potential advantages are understood by referring to FIGS. 1 through 5 of the drawings. In this document, like reference signs denote like parts or steps.

Figure 1:
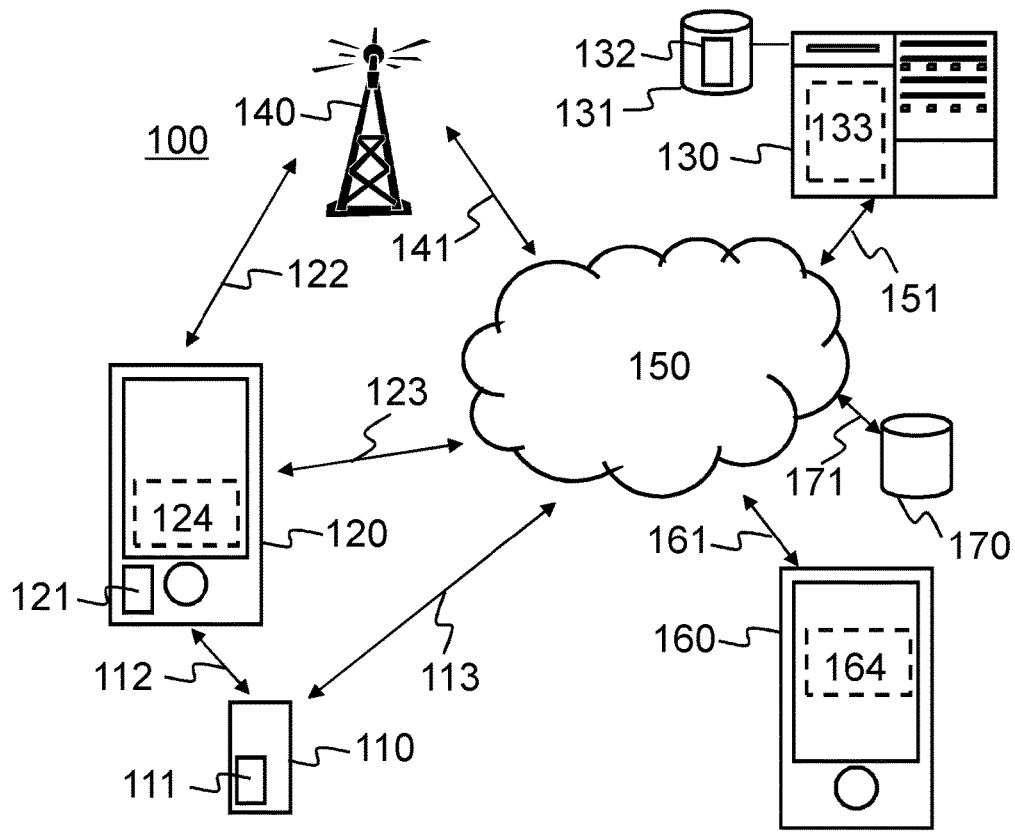
FIG. 1 shows a schematic drawing of a system of an example embodiment.

FIG. 1 shows a schematic picture of a system 100 according to an example embodiment of the present disclosure.

The system comprises a client device 120 that may comprise a multimedia device, a mobile phone, an Internet tablet or a laptop computer, for example. The client device 120 is capable of downloading and locally executing software program code. The software program code may be a proprietary client application 124 of a service whose server application 133 is running on the server apparatus 130 of the system 100. The client device 120 may comprise a metadata element 121 for creating data usable as metadata relating to event entries of the proprietary application 124, such as an electronic diary of a participant participating a clinical trial.

The metadata element 121 may comprise at least one of the following: a microphone, a positioning device for determining the current location of the participant apparatus 120, and a local clock. The client device 120 is configured to be connectable to a wireless communication network 140 over a wireless connection 122. The wireless connection 122 may comprise a mobile cellular network or a wireless local area network (WLAN), for example. The wireless communication network 140 may be connected to a public data communication network 150, for example to the Internet, over a data connection 141. The proprietary application 124 may be operable also in offline mode and there is no need to have online connection over the network to the server 130, 131 all the time. In offline mode, the client device 120 may store application related data to cache memory and update the data to the server 130, 131 once getting the online access or at least one of the subject user, the proprietary application or the server application triggers or requests to synchronize or upload data, for example.

In an embodiment, the system 100 comprises a personal device 110 configured to be capable of capturing clinical trial related data. The personal device 110 may comprise storage 111 for the trial related data. The storage 111 may comprise a flash memory card, for example. The personal device 110 is configured to be connectable to the client device 120 over a data connection 112. The data connection 112 may be a wired connection or a wireless connection. The wired connection may comprise Universal Serial Bus (USB), High-Definition Multimedia Interface (HDMI) or local area network (LAN), for example. The wireless connection may comprise Bluetooth™, Radio Frequency Identification (RF-ID) or wireless local area network (WLAN), for example.

The personal device 110 is configured to send captured data over the data connection 112 to the client device 120. Such transmittal may be initiated by a participant of the personal device 110, by a participant of the client device 120, or automatically based on settings. Such settings may comprise for example time of the day, amount of newly captured clinical trial related data or existence of the data connection 112 for the personal device 110.

In an embodiment, a subject user of a clinical trial may utilise a client device 120 for generating and transmitting clinical trial related data to a server apparatus 130, 131. Additionally, a personal device 110 may be used but not necessarily.

The clinical trial related data may be sent from the client device 120 to the system server 130. At the system server 130, the received data may be analysed, corrected and processed further according to the clinical trial rules and regulations.

Clinical trial related data may comprise at least one of the following:

clinical trial data of a subject user, based on an electronic diary or study of a subject user, for example; and pre-clinical trial data of the subject user, such as registering data for the subject user, consenting data for the subject user or re-consenting data for the subject user, for example. Re-consenting may be needed if clinical trial protocol is changed, for example.

In an embodiment, a client device 120 is setup for the subject user of the clinical trial. A proprietary application of the client device comprises a client application of a clinical trial service. The client application may be configured to carry out steps relating to the clinical trial related data.

In an embodiment, the proprietary application 124 may comprise a plurality of client applications. A first client application may comprise an electronic consenting application comprising login/setup process according to embodiments disclosed. Such electronic consenting application may be used before the actual clinical trial begins for the subject user. A second client application may comprise a data capturing application of the clinical trial for the subject user.

In an embodiment, a first client application may comprise a registration application for a subject user. In response to the subject user registration is completed, a second client application may be downloaded or pushed to the client device. The second client application may comprise, for example, consenting and/or data capturing application provisioned for the clinical trial that the subject user is assigned to.

In an embodiment, Single Sign-On (SSO) may be used for access control or subject user identifying for at least one client application. The SSO may also relate to a non-proprietary application.

In an embodiment, a client application may comprise a browser application configured to carry out steps to configure and setup the client device for the subject user according to embodiments disclosed.

In an embodiment, a client application may comprise a setup application configured to carry out steps to configure and setup the client device for the subject user according to embodiments disclosed. Once the setup is done, a second client application, such as a web browser, may be taken into use.

Any of the proprietary application related embodiments may be used independently, combined or selectively combined, but not limited to the disclosed embodiments. No matter proprietary application is used, the proprietary application may be also be understood as a client application (such as a browser) configured to be used for a proprietary purpose, such as for setting up a client device for the subject user, for example.

In an embodiment, "Bring Your Own Device" (BYOD) may be used by the subject user as the client device. BYOD device allows the subject user in a clinical trial to use their own computer devices to access and respond to study related questionnaires. BYOD device may comprise, for example, a smart phone, a laptop, a desktop PC, a user wearable smart device or an Internet enabled TV.

In an embodiment, in BYOD case, the client device may be already authorized for the subject user before registering or consenting for a clinical trial. A proprietary application may be provisioned in a second device and after provisioning the proprietary application within the second device, the proprietary application may be sent to the client device, the BYOD device in this case, for the subject user. Subject credentials can be sent to the BYOD device encrypted, using public key cryptography, for example.

In an embodiment, a kiosk mode device may be used by the subject user as the client device 120. The kiosk mode may comprise, for example, a kiosk application 124 run in the client device 120 providing a mechanism for a yes/no prompt on a kiosk application screen online. Another mechanism is inputting consent form at the kiosk application screen online, letting the subject user to sign it and feed it back into the kiosk mode, e.g. within the electronic diary. Regardless of the method of signing, the consent obtained is digitally stored in the consent database and the consent event is recorded in the system.

In an embodiment, a kiosk mode device may be used in a coordinator mode using coordinator credentials and in a subject user mode using subject credentials regardless of what applications, proprietary application and/or any kind of client applications as disclosed in different embodiments, are executed in the kiosk mode device.

The subject user may be a human or an animal. In case of the animal, an owner of the animal may operate the client device 120 and provide necessary interaction with the system 100 or the animal may be wearing a personal device 110, for example.

In an embodiment, the system 100 comprises a server apparatus 130, which comprises a storage device 131 for storing clinical trial related information, such as electronic diary data, event logs and metadata received over a data connection 151, user profile information of participants, credentials, history information of participants, clinical trial information, consenting data, registration data, client software application data and server software application data, for example.

In an embodiment, the system 100 may further comprise other participant apparatuses 160, connected to the network 150 over connection 161, wherein tasks relating to the service system may be processed. The participant apparatus 160 may comprise the participant apparatus of a coordinator or administrator of the clinical trial, for example.

Different apparatuses 110, 120, 130, 160, 170 may provide clinical trial related information to be maintained in the service system 100. The information may be maintained as a collaborative clinical trial record 132 within the server apparatus 130, 131. The collaborative record 132 may comprise any trial related information provided by different participants, the service system or sensors, for example.

Furthermore, the coordinator of an apparatus 160 may define trial targets and recommendations. The system service 130, 131 and its server application 133 may receive participant data and/or an event log relating to clinical trial generated by the proprietary application 124 of the client device 120 as input and process the received data.

In an embodiment, a server apparatus 130 maintains, by a service provider such as a sponsor or organizer of the clinical trial, the service system data, such as clinical trial related records. Each record may be identified using a unique identifier. Furthermore, a subject user identifier may be used to identify each subject user. The subject user identifier may comprise, for example a unique number, string or an email address, for example. In general, participant identifier must be unique but not something based on which someone can recognize or identify the user.

Information relating to clinical trial records, or event logs corresponding to event entries of an electronic diary, or any other participant related data, may be transmitted to the server 130 from a plurality of apparatuses 110, 120, 160 over the network 150. Eventually, the received service data is maintained, by an operator, at the server 130 comprising storage device 131, wherein the data being available for participants having access to that particular record. Furthermore, metadata associated with the service data may also be stored in the server 130 or storage device 131, such as location information, time information, or a device identifier, for example.

In an embodiment, clinical trial related data generated by a participant may be transferred to a server apparatus 130 over different paths. A first path may comprise sending data captured by a proprietary application (e.g. a clinical trial client application) of a client device 120 over a wireless communication network 122, 140, 141 and public data communication network 150, 151 to the server apparatus 130. A second path may comprise sending data captured by a default application (e.g. a browser) of a client device 120 over a wireless communication network 122, 140, 141 and public data communication network 150, 151 to the server apparatus 130. A third path may comprise sending data captured by a personal device 110 (such as user wearable sensor) to the client device 120 over connection 112 and therefrom over a wireless communication network 122, 140, 141 and public data communication network 150, 151 to the server apparatus 130. A fourth path may comprise sending data captured by the device 110 to a computer apparatus 120 and therefrom over the connection 123 and the public data communication network 150, 151 to the server apparatus 130.

In an embodiment, the proprietary application in the client device 120 may be a client application of a service whose server application is running on the server apparatus 130 of the system 100. The proprietary application may capture the data for the first path. Also metadata for the captured multimedia may be retrieved by the proprietary application from the metadata elements 121 of the client device 120. For the second path, the data captured by the default application may be imported to the proprietary application before transmitting to the server apparatus 130. The proprietary application may check the data and extract and apply metadata for the data. For the third path, the data may be captured by the external device 110 and transmitted to the proprietary application of the client device 120 for sending to the server apparatus 130. The proprietary application may check the data and extract and apply metadata for the multimedia data. A participant may provide additional metadata using the client device 120. For the fourth path, the data may be captured by the external device 110 and transmitted to a communication application of a computer apparatus 120. The communication application may check the multimedia data and extract and apply metadata for the multimedia data. The participant may provide additional metadata using the computer apparatus. In a further embodiment, the participant may access the data on the server apparatus and provide additional metadata.

In an embodiment, a proprietary or client application 164 in the user apparatus 160 (e.g. administrator apparatus) may be an administrator application of a service whose server application is running on the server apparatus 130 of the system 100.

In an embodiment, the personal device 110 may comprise a user wearable device communicating with the apparatus 120 over a local connection 112. The local connection 112 may comprise, for example, at least one of the Bluetooth, Radio Frequency Identification (RF-ID), near field communication (NFC) or other wireless non-cellular connection. The wireless non-cellular connection may comprise industrial, scientific and medical (ISM) radio bands that are radio bands (portions of the radio spectrum) reserved internationally for the use of radio frequency (RF) energy for industrial, scientific and medical purposes, for example. The local connection 112 may also comprise non-RF connection, such as Light Fidelity (Li-Fi), for example. Alternatively, the user wearable device 110 may be comprised by the apparatus 120, as illustrated by an integrated apparatus 120-121. The user wearable device 110 may also comprise a wearable garment. The apparatus 110, 120 may be for example a wrist wearable user apparatus.

In an embodiment, the personal device 110, such as a user wearable device, may be paired with the client device 120. Pairing may be based on device identifiers of the devices 110, 120 and pairing information may be maintained within the subject user profile associated with the subject.

Furthermore, the personal device 110 may be connected to the network 150 over local connection 113 corresponding to connection 123, for example.

In an embodiment, a communication interface module of the device 120 may comprise location modules for tracking location of the portable apparatus 120. Such location modules may comprise a module for providing a connection to satellite based global positioning system (e.g. GPS, not shown), a module for cellular based positioning system, a module for wireless non-cellular positioning system (e.g. Wi-Fi) or a module for hybrid positioning system, for example. The positioning system may also be used for user speed detection, altitude detection, route detection and route planning for various embodiments.

In an embodiment, the client device 120 may be connected over a wireless or wired connection to a wide area network 150, such as Internet. Router apparatuses (not shown) may be used for providing the access to a wide area network 150. The access may comprise cellular or non-cellular connection.

In an embodiment, a proprietary application 124 in the device 120 may be a client application of a service whose server application is running on the server apparatus 130 of the system 100. The proprietary application 124 may capture the user input data for the service and provide the user output data from the service.

The server 130 may also provide a cloud service for the portable device 120 data. Optionally, further apparatuses may be added, such as peripheral devices for maintaining, providing or processing the portable device 120 data and communication devices for connecting the peripheral devices to the system 100.

In an embodiment, the system 100 may further comprise an external database 170. The external database 170 may be accessible to the network 150 over connection 171. The database 170 may have corresponding structure as the server apparatus 130, 131, for example.

An electronic diary is a tool used during a clinical trial to register assessment of a participant's condition (e.g. symptom severity, quality of life) by the participant. The electronic diary registers data in a storage device and allows for automatically monitoring the time the entry was made. Frequent recording of symptoms using a diary helps to reduce recall bias. Electronic diaries enable entries are made as scheduled, and not, for example, in a batch immediately before the clinic visit. Electronic diaries also enable finding out if a participant takes the medication according to the treatment schedule, which is important during clinical trials. Investigators, on the other hand, are assessing the received data that was registered by the electronic diary.

In an embodiment, information relative to a clinical trial between a client device 120 operable by a plurality of users and a server apparatus 130 is transceived. The client device 120 and the server apparatus 130 are configured to communicate via a data network 150. A proprietary application 124 of the client device 120 is a client application of a clinical trial service whose server application 133 is running on the server apparatus 130, wherein a coordinator user profile associated with coordinator credentials and a subject user profile associated with subject credentials are maintained by the server application 133 at the server apparatus 130. The proprietary application 124 may comprise, for example, the electronic diary tool or any kind of client application as disclosed in different embodiments, such as an electronic consenting application, for example.

The coordinator credentials may be received via a user interface by the proprietary application 124, 164, and the coordinator credentials accepted in response to determining the coordinator credentials being authorized credentials, and logging in the coordinator user by providing coordinator level access to the proprietary application 124, 164.

Furthermore, coordinator input data may be received by the proprietary application 124, 164 configured to trigger user change for the client device 120. A request may be generated and sent by the proprietary application 124, 164 in response to the coordinator input data, to the server application 133 indicating the triggered user change.

In an embodiment, coordinator input data may be received by the proprietary application 124 configured to trigger user change within the client device 120. A request may then be automatically generated and sent by the proprietary application 124 to the server application 133 indicating the triggered user change. In response to the request, subject credentials may be received by the client device 120, for example.

In an embodiment, coordinator input data may comprise any input data indicating user change for the client device, setup for the client device, setup for the proprietary application or merely exit function (trigger "exit" via user interface) by the coordinator to close the coordinator session and initiate subject user login, for example.

Then again, subject credentials may be received by the proprietary application 124 from the server application 133, wherein the subject credentials are associated with the subject user profile generated by the server application 133. The coordinator user may be logged out by disconnecting coordinator level access to the proprietary application 124 and resetting the coordinator credentials and session data within the client device 120, and the subject credentials may be stored by the proprietary application 124 for automatic first logging in of the subject user.

In an embodiment, the request may be sent, in response to the coordinator input data, by the proprietary application 124 to the server application 133 indicating the triggered user change and comprising an identifier for the subject user.

An electronic diary may comprise a computer-implemented client software application for a participant of a clinical trial to record data for the clinical trial. The electronic diary may also comprise a computer-implemented web browser application. The electronic diary may also comprise a combination of a client software application and a browser application.

The electronic diary allows only registered participant to record data. Typically, the electronic diary may remind the participant to fill in data at scheduled time according to a trial protocol and may present only questions the participant should answer at that time, for example. In addition, the electronic diary may time stamp the recorded data and maintain an audit trail of changes to the data in order to ensure the integrity and validity of the clinical trial related data.

The use of electronic diaries is regulated by laws and guidelines from local authorities as well as GCP (Good Clinical Practice). These regulations typically require that clinical trial participants are authenticated prior to entering the proprietary application 124, such as electronic diary, to ensure that participant privacy is not compromised and to ensure that the data is recorded by the participant and not by someone else. Secure subject user credentials may be generated and allocated by the server application 133 running at the server apparatus 130.

In an embodiment, the proprietary application 124 may require login identification information to participants allowed to use the proprietary application 124. The identification information may comprise credentials, such as a participant login name and an associated password. The term "participant" refers to a person (such as e.g. a subject user, a guardian of the subject user, a care giver of the subject user, or an observer of the subject user or an animal, for example) using the proprietary application 124, such as an electronic diary, to record and submit participant-reported data (such as participant diary data or other related clinical data, or a person (e.g. a subject user) receiving information regarding a clinical trial during an electronic informed consent session, for example) for use in clinical trials run by pharmaceutical industry, for example. Typically, the participant needs to be registered before allowed in the clinical trial. The participant may utilize an electronic diary 124 within a client device 120 (such as a smart phone, a personal digital assistant, a tablet or a laptop computer, for example) to record and send participant data.

In an embodiment, registration of a subject user for the clinical trial may take place before consenting of the subject user, or together with the consenting session. Registration and/or consenting can also take place when the clinical trial starts, for example when the subject user gets the client device to be used for the clinical trial and/or consenting. Registration and/or consenting may be carried out using a proprietary application comprising a client application, a client plugin or a client web session, for example.

In an embodiment, a client device 120 may be used by a plurality of participants. In such case the client device 120 may generate event entries or other clinical trial related data by different users to be transmitted to the server 130, 131 using the same client device identifier. When handing the client device 120 from first user (e.g. coordinator) to second user (e.g. subject user), the first user's session data needs to be reset and credentials for the second user easily and securely provided.

Participant data and an identifier of the participant are received at a participant data collector server 130, 131 by the server application 133. The participant data is entered by the participant using the client device 120 or a personal device 110 without user input. Thus, the participant data is recorded by the proprietary application 124 that sends the participant data to the server application 133. The personal device 110, such as a wearable device, may independently send data to the server 130, 131 or to the proprietary application 124, to be appended to the participant data. In case the personal device 110 sends independently the data to the server 130, 131, the personal device may transmit an event log corresponding to event entries of an electronic diary of a participant of a clinical trial, wherein the event log is generated in the personal device, and the event log comprising an event identifier and an event timestamp for at least one event entry that can be associated to participant data for investigation at the server 130, 131 based on a device identifier or participant identifier, for example.

A typical clinical trial begins with the construction of a clinical protocol that describes how a trial is to be performed, what data elements are to be collected, and what medical conditions need to be reported immediately to the pharmaceutical sponsor and the regulatory authority, such as Food and Drug Administration (FDA) in the USA, for example. The clinical protocol and its author are the ultimate authority on the conduct of the clinical trial. This protocol is the basis for every action performed by multiple players in diverse locations during the entire conduct of the trial. Any deviations from the protocol specifications, no matter how well intentioned, threaten the viability of the data and its usefulness for the regulatory authority, such as Food and Drug Administration (FDA) submission in the USA, for example.

Participant compliance is important for a clinical trial. Participant may be required to take medication and follow the regimen at times specified by the protocol. Additionally, an electronic diary is filled to provide participant data at times specified by the protocol. For instance, the protocol may specify that the participant needs to take certain drug at certain times. The protocol may define, for example, that certain drug should be taken on Day1 and report symptoms on Day2 and again on Day3, Day4, Day5, etc., each entry with their own date/timestamp.

Consent to participate in a clinical trial should be obtained. A list of registered users may be provided with consent information. Furthermore, for whom consent was obtained can be outputted and forwarded to an entity involved in the clinical trial. Typically, this is a drug company.

Because participant confidentiality is important, anonymity of a person meeting the specified criteria must be preserved. The process of obtaining consent may include meeting specified criteria for approval to participate in the clinical trial.

In an embodiment, the method can first include the steps of obtaining consent or authorization of the prospective participant, obtaining identifying information from the prospective participant, and generating personal identifying information, for example. The personal identifying information can comprise biometric data and information.

Secure setting up a client device 120 for clinical trial related information, such as consenting, re-consenting or the clinical trial subject user data, has certain problems or drawbacks. Method for providing credentials, such as a username and a password may not be universally convenient or successful for every participant as there could be number of complications. One may not have an email account, a printer may not be available or it simply can lack paper or ink etc. Again, the password generated may be long, complex and characters may be difficult to distinguish from each other (I, l, 1; O, 0; vvvv, ww, for example), thus making the input of the credentials tedious and cumbersome. Also, the client device 120 in use, especially if a touch device in question may be a new experience (as a device type) to a subject user, making the data input event of username and password even further difficult to execute.

Re-consenting may be needed, for example, if the clinical trial protocol or the original consent is invalid or there has been a substantial change to the research or trial protocol or to the subject user's condition since the time of the original consent, such that research participation may no longer be consistent with the subject's preferences and interests and the subject may need to reconsider the decision.

Typically, clinical trial including needed consenting steps may last for years. Thus, the client device used by the subject user may become obsolete, break down, or have some malfunctions during that time. It may be that the client device cannot be repaired, for example due to lack of spare parts, such as batteries. In such case, for example, the embodiments disclosed enable setting up the replacement client device.

Furthermore, a subject user in device handover situation may find using the device difficult due physical attributes of the user. For example, fingers may be too large compared to active areas on screen, keyboard keys are too small for a finger, coordination of movement of fingers is difficult due to a disease (e.g. Parkinson's disease) or similar condition.

Further problems may relate to password/username, such as an unfamiliar or strange character may be difficult to locate in a keyboard or it may be difficult for the subject user to see and understand different user interfaces and states of the user interface, e.g. when a key is pressed the key changes from inactive to active state. Other usability challenges may exist relating to virtual keyboard, Caps Lock, and disturbing notifications presented to the user, for example.

Only exemplary problems are mentioned to illustrate the challenges for the subject user to fill in secure user credentials for the proprietary application 124 to transceive clinical trial related data(pre-trial, on-trial or post-trial).

The problem is evident and disturbing mostly in user experience perception of the service, hence rendering the overall service difficult or slow to use. Limiting the problem as much as possible would allow clear benefit for service provider and subject user as more efficient, easier to use and faster clinical trial data transceiving between the proprietary application 124 and the service application 133.

Figure 2:
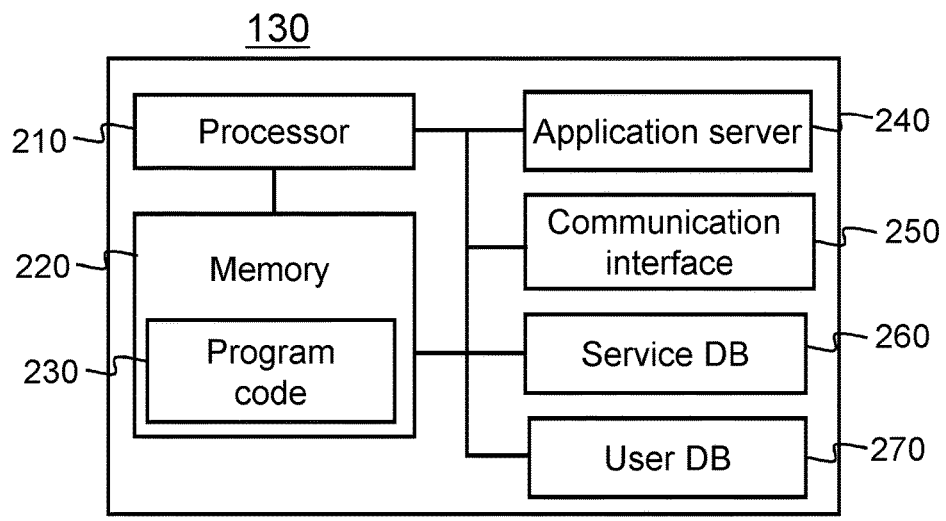
FIG. 2 shows a block diagram of the server apparatus of an example embodiment.

FIG. 2 presents an example block diagram of a server apparatus 130 in which various embodiments of the invention may be applied. All elements described in FIG. 2 are not necessary to be implemented in the same apparatus 130.

The general structure of the server apparatus 130 comprises a processor 210, and a memory 220 coupled to the processor 210. The server apparatus 130 further comprises software 230 stored in the memory 220 and operable to be loaded into and executed in the processor 210. The software 230 may comprise one or more software modules and can be in the form of a computer program product. The software 230 may comprise a server application 133 of FIG. 1.

The processor 210 may be, e.g., a central processing unit (CPU), a microprocessor, a digital signal processor (DSP), a graphics processing unit, or the like. FIG. 2 shows one processor 210, but the server apparatus 130 may comprise a plurality of processors.

The memory 220 may be for example a non-volatile or a volatile memory, such as a read-only memory (ROM), a programmable read-only memory (PROM), erasable programmable read-only memory (EPROM), a random-access memory (RAM), a flash memory, a data disk, an optical storage, a magnetic storage, a smart card, or the like. The server apparatus 130 may comprise a plurality of memories. The memory 220 may be constructed as a part of the server apparatus 130 or it may be inserted into a slot, port, or the like of the server apparatus 130 by a participant. The memory 220 may serve the sole purpose of storing data, or it may be constructed as a part of an apparatus serving other purposes, such as processing data.

The communication interface module 250 implements at least part of data transmission. The communication interface module 250 may comprise, e.g., a wireless or a wired interface module. The wireless interface may comprise such as a WLAN, Bluetooth, infrared (IR), radio frequency identification (RF ID), GSM/GPRS, CDMA, WCDMA, LTE (Long Term Evolution) or 5G radio module, for example. As the radio technologies are evolving and new replacing systems being developed, the new developed technologies can be used for the communication interface module 250 in view of different embodiments disclosed. The communication interface module 250 may also comprise non-RF connection, such as Light Fidelity (Li-Fi). The wired interface may comprise such as Ethernet or universal serial bus (USB), for example.

The communication interface module 250 may be integrated into the server apparatus 130, or into an adapter, card or the like that may be inserted into a suitable slot or port of the server apparatus 130. The communication interface module 250 may support one radio interface technology or a plurality of technologies. Configuration information between the client device 120 and the system server 130 may be transceived using the communication interface 250. Similarly, account creation information between the system server 130 and a service provider may be transceived using the communication interface 250.

An application server 240 provides application services e.g. relating to the participant accounts stored in a participant database 270 and to the service information stored in a service database 260. Different application services may be provided to different users, such as the first user (client participating the clinical trial), the second user (coordinator/administrator of the trial) and the third user (sponsor of the trial). The application server 240 may comprise a server application 133 of FIG. 1.

A skilled person appreciates that in addition to the elements shown in FIG. 2, the server apparatus 130 may comprise other elements, such as microphones, displays, as well as additional circuitry such as input/output (I/O) circuitry, memory chips, application-specific integrated circuits (ASIC), processing circuitry for specific purposes such as source coding/decoding circuitry, channel coding/decoding circuitry, ciphering/deciphering circuitry, and the like.

Figure 3:
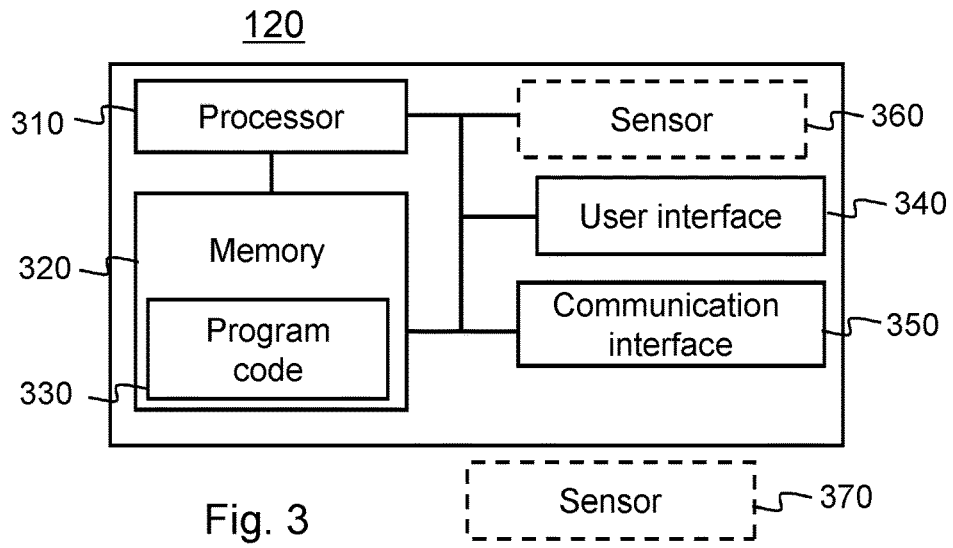
FIG. 3 shows a block diagram of a client device of an example embodiment.

FIG. 3 shows a block diagram of a client device 120 of an example embodiment. In an embodiment, a sensor 360, 370 may be implemented as a separate device 370 communicating via the communication interface 350 with the client device 120, or as an integrated sensor 360 within the device 120. The user interface 340 may be implemented also in another device connected via a communication interface 350 to the device 120. Such device may comprise a mobile phone, a smart phone, or a tablet, for example. In an embodiment, the device 120 may communicate with a plurality of sensors 360, 370, both internal and external sensors, and of a plurality of participants. In an embodiment, the sensor 360 may also comprise a camera for capturing multimedia data to be submitted to the server apparatus 130, 131 as participant data, event data for the clinical trial, for determination of preliminary trauma information or for creating multimedia data, for example.

The general structure of the device 120 comprises a user interface 340, a communication interface 350, a processor 310, and a memory 320 coupled to the processor 310. The device 120 further comprises software 330 stored in the memory 320 and operable to be loaded into and executed in the processor 310. The software 330 may comprise one or more software modules and can be in the form of a computer program product. Not all elements of FIG. 3 are necessary but optional for the portable apparatus 120, such as the sensor 360, 370.

In an embodiment, a proprietary application 124 of FIG. 1, such as an electronic diary, an electronic consenting application or an electronic registration application, is a computer-implemented client software application 330 for a subject user of a clinical trial to record data for the clinical trial. The proprietary application may also comprise a computer-implemented web browser application. The electronic diary may also comprise a combination of a client software application and a browser application.

The processor 310 may be, e.g., a central processing unit (CPU), a microprocessor, a digital signal processor (DSP), a graphics processing unit, or the like. FIG. 3 shows one processor 310, but the device 120 may comprise a plurality of processors.

The memory 320 may be for example a non-volatile or a volatile memory, such as a read-only memory (ROM), a programmable read-only memory (PROM), erasable programmable read-only memory (EPROM), a random-access memory (RAM), a flash memory, a data disk, an optical storage, a magnetic storage, a smart card, or the like. The device 120 may comprise a plurality of memories. The memory 320 may be constructed as a part of the device 120 or it may be inserted into a slot, port, or the like of the device 120 by a user. The memory 320 may serve the sole purpose of storing data, or it may be constructed as a part of an apparatus serving other purposes, such as processing data.

The user interface 340 may comprise circuitry for receiving input from a user of the device 120, e.g., via a keyboard, a touchpad, a motion sensor, a touch-screen of the device 120, speech recognition circuitry, gesture recognition circuitry or an accessory device, such as a headset or a remote controller, for example. Furthermore, the user interface 340 may comprise circuitry for providing output for the user via a display, a speaker, a touch-sensitive display or a tactile feedback device, for example.

In an embodiment, a user may speak during the clinical trial when generating electronic consent or electronic diary relating to sensations during the trial and the speech is automatically converted to feedback information for the system. Thus feedback is always up-to-date and accurate.

The communication interface module 350 implements at least part of data transmission. The communication interface module 350 may comprise, e.g., a wireless or a wired interface module. The wireless interface may comprise such as a WLAN, Bluetooth, infrared (IR), radio frequency identification (RF ID), NFC, GSM/GPRS, CDMA, WCDMA, LTE (Long Term Evolution) or 5G radio module. As the radio technologies are evolving and new replacing systems being developed, the new developed technologies can be used for the communication interface module 350 in view of different embodiments disclosed. The communication interface module 350 may also comprise non-RF connection, such as Light Fidelity (Li-Fi). The wired interface may comprise such as universal serial bus (USB), for example. The communication interface module 350 may be integrated into the device 120, or into an adapter, card or the like that may be inserted into a suitable slot or port of the device 120. The communication interface module 350 may support one radio interface technology or a plurality of technologies. The communication interface module 350 may support one wired interface technology or a plurality of technologies. The device 120 may comprise a plurality of communication interface modules 350.

In an embodiment, the communication interface module 350 may comprise location modules for tracking location of the device 120. Such location modules may comprise a module for satellite based global positioning system (e.g. GPS), a module for cellular based positioning system, a module for wireless non-cellular positioning system (e.g. Wi-Fi) or a module for hybrid positioning system, for example.

In an embodiment, the communication interface 350 with a satellite based global positioning system (e.g. GPS) may detect altitude of the participant to provide an estimate of thinness of air. Such estimate of air thinness may be used as input for determining characteristics of the event for the electronic diary.

A skilled person appreciates that in addition to the elements shown in FIG. 3, the device 120 may comprise other elements, such as microphones, speakers, sensors, cameras, as well as additional circuitry such as input/output (I/O) circuitry, memory chips, application-specific integrated circuits (ASIC), processing circuitry for specific purposes such as source coding/decoding circuitry, channel coding/decoding circuitry, ciphering/deciphering circuitry, and the like. Additionally, the client device 120 may comprise a disposable or rechargeable battery (not shown) for powering when external power if external power supply is not available.

In an embodiment, the client device 120 comprises speech or gesture recognition means. Using these means, a predefined phrase or a gesture may be recognized from the speech or the gesture and translated into control information for the device 120.

In an embodiment, the disclosed solution automatically takes care of manual login procedure on behalf of the subject user.

A site coordinator may log in, and create or pick ready-made account credentials (username and password) for the subject user via the proprietary application 124. The selected credentials are received from the server application 133. The coordinator may then log off manually or is logged off automatically. The created subject user credentials are not cleared from the client device memory 320 but are saved for optionally recovery purposes and especially for the login step of the subject user. The login step can automatically use the received subject user credentials for logging in and authentication on behalf of the subject user.

In case of auditing or due to other reasons, if for example regulations prevent or discourage automatic logging in, the subject user may be provided with a "log in" function or touch sensitive key on the user interface 340 to be triggered in order to record, indicate or control the exact time when the subject interaction started. Another reason for leaving the "log in" function triggering to the subject user may be the use of digital signing, e.g. by fingerprint sensor 360, 370, prior to or during logging in, wherein the signing by subject user's fingerprint may be used in later phases of the clinical trial process.

Alternatively, if the client device 120 is known to be used only in controlled or on restricted areas, premises, situation or network, then default or automated set-up procedure could be applied. Here, an active coordinator contribution is not necessarily required otherwise but only to put the client device 120 available for the subject user to pick it up for the clinical trial. The client device 120 could allow, by the proprietary application 124, simple automatic or manual function of "create new user" or "pick from list" relating to the subject user. In simplest form, the subject user can make or initiate the setup simply by taking the client device 120 into use. Taking the client device 120 into use could be based on event such as: movement of the client device 120 (e.g. pitch, yaw, roll, moving in x-y-z coordinate space), powering-up, launching an application (e.g. proprietary application 124), activating an application (e.g. proprietary application 124), manipulating application (e.g. proprietary application 124) or client device 120 control items such as button, enablement of client device 120 network connection or physical positioning (coordinates). After the set-up action, the client device 120 with an application (e.g. proprietary application 124) could provision the subject user automatically as an authenticated user for the clinical trial.

Figure 4:
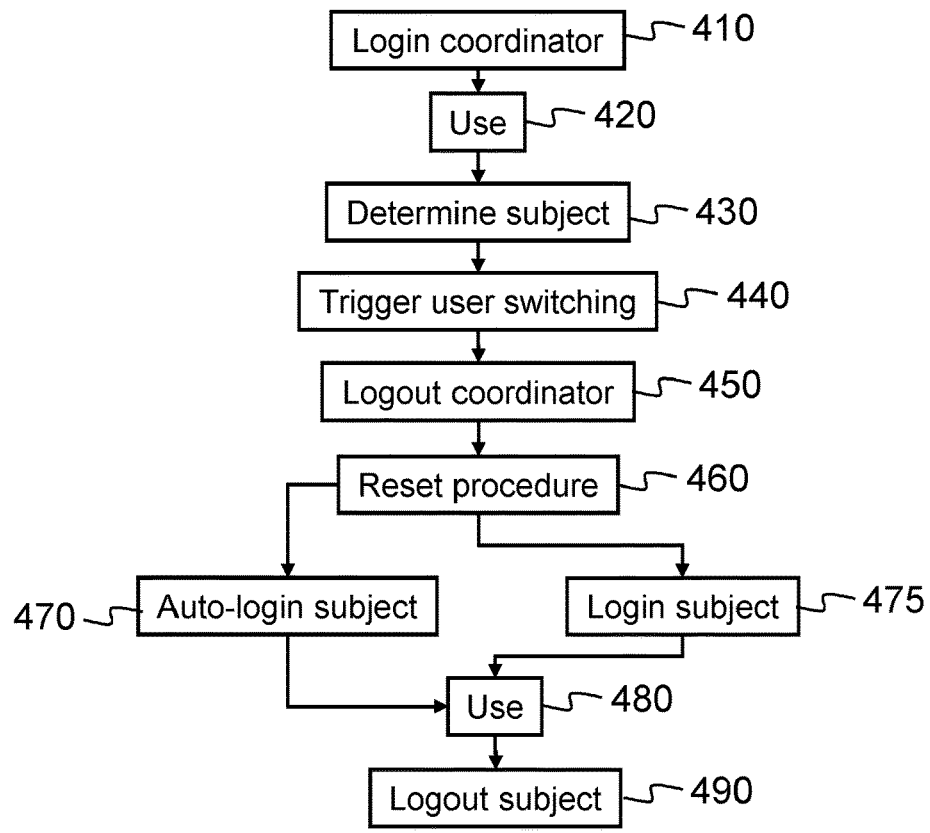
FIG. 4 shows a flow chart of operations according to an example embodiment of the invention.

FIG. 4 shows a flow chart of operations according to an example embodiment of the invention.

First in step 410, coordinator credentials are received via a user interface 340 of the client device 120 by the proprietary application 124, and the coordinator credentials are accepted in response to determining the coordinator credentials being authorized credentials, and logging in the coordinator user by providing coordinator level access to the proprietary application 124.

Second in step 420, the coordinator is logged in for using the proprietary application 124 with coordinator access rights and may trigger administrative tasks and processes relating to subject users and the clinical trial data.

Third in step 430, a subject user may be determined and subject user's username and password may be fetched from the server application 133 (backend system) while the coordinator user is logged in and working on the client device 120.

Fourth in step 440, the coordinator user activates the automatic switch procedure, so that the coordinator user session information is cleared 460 from the client device 120 and/or the server application 133 (backend system), while the subject user information (username and password) are kept on the client device 120.

In an embodiment, the proprietary application 124 may go to default state (login view, for example) when the coordinator logs out in step 450. The subject user's username and password can be used to automatically pre-fill the login input fields (username and password) or used in direct network login request to the server application 133 of the backend system.

Order of logout of coordinator 450 and reset procedure 460 to reset coordinator session data may vary and they can be performed in any order or simultaneously.

Keeping the subject user's username and password in the system can be done in practice by storing them on the client device 120 persistent storage 320 and/or kept in application 330 or device memory. Using these credentials automatic login procedure 470 can be done by creating a login request to the server 130 and the server application 133.

The proprietary application 124 may go to default state (login view, for example) after coordinator logout step 450. The kept subject user's username and password may be used to pre-fill the login input fields (username and password) for login step 475 or used in direct network login request 470 to the backend system.

In an embodiment, the subject user can manually press a login button with the pre-filled username and password input fields as in step 475 if completely automated end-to-end login process 470 is not desirable.

In step 480, the subject user is logged in, i.e. authenticated, and continue using the client device 120 and the proprietary application 124 for the clinical trial until logging out the subject user as in step 490.

In an embodiment, steps 410-440 may correspond to manual interactions between the coordinator and the proprietary application 124, steps 450-470 to automatic interactions by the service system and/or the proprietary application 124, and steps 475-490 to manual interactions between the subject user and the proprietary application 124.

In an embodiment, an alternative solution of operations is where the coordinator user steps 410-470 are automated by the system.

In such embodiment, the coordinator user provides the client device 120 to be available for use in a designated area. A subject user may then take the client device 120 into use and credentials, such as username and password are fetched from the proprietary application 133 of the backend system. This can be done prior or while the subject user takes the client device 120 into use or while the subject user is already using the client device 120.

The subject user can manually activate the automatic login procedure (e.g. by pressing a button with text: "start") or it can be initiated automatically as the client device 120 is taken into use.

Optionally, the subject user can manually press the login button with pre-filled username and password input fields if completely automated end-to-end login process is not desirable.

Stored credentials of the subject user comprising username and password can be used to pre-fill the login input fields (username and password) or used in direct network login request to the server application of the backend system and no manual interaction is required from the subject user. Then, the subject user is logged in, i.e. authenticated, and the subject user may continue using the client device 120 and the proprietary application 124.

In an alternative version described above, the coordinator user could also verify after logout of each subject user that the client device 120 is still operational and optionally reset the client device 120 for new use. Here it would be possible also that the subject user credentials are created beforehand for the next subject user.

Figure 5:
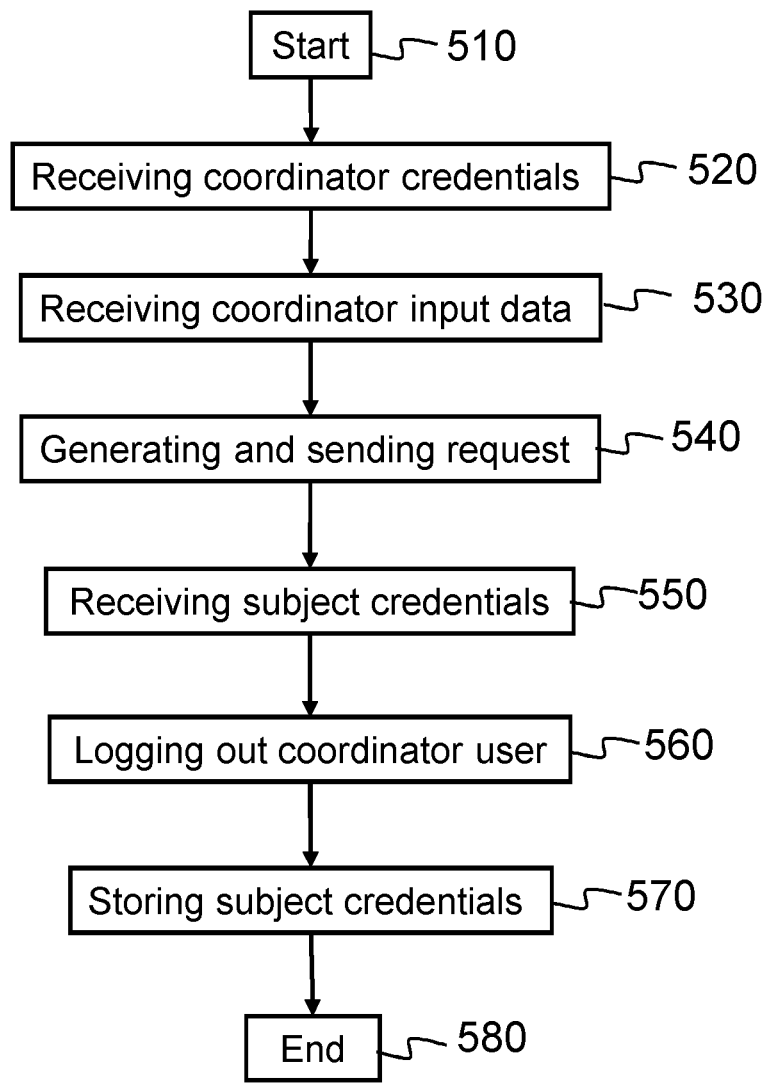
FIG. 5 shows a flow chart of a process of an example embodiment.

FIG. 5 shows a flow chart of a process according to an example embodiment of the invention.

A computer implemented method starts in step 510. The computer implemented method is suitable for transceiving clinical trial related information between a client device operable by a plurality of users and a server apparatus, wherein the client device and the server apparatus are configured to communicate via a data network. A proprietary application of the client device may be a client application of a clinical trial service whose server application is running on the server apparatus, wherein a coordinator user profile associated with coordinator credentials and a subject user profile associated with subject credentials are maintained by the server application at the server apparatus.

In step 520, the coordinator credentials are received via a user interface by the proprietary application, the coordinator credentials are accepted in response to determining the coordinator credentials being authorized credentials, and the coordinator user is logged in by providing coordinator level access to the proprietary application.

In step 530, coordinator input data is received by the proprietary application configured to trigger user change for the client device.

In step 540, a request is generated and sent by the proprietary application in response to the coordinator input data to the server application indicating the triggered user change.

In step 550, subject credentials are received by the proprietary application from the server application, wherein the subject credentials being associated with the subject user profile generated by the server application.

In step 560, the coordinator user is logged out by disconnecting coordinator level access to the proprietary application and resetting the coordinator credentials and session data within the client device.

In step 570, the subject credentials are stored by the proprietary application for automatic first logging in of the subject user.

In step 580, the method ends.

Without in any way limiting the scope, interpretation, or application of the claims appearing below, a technical effect of one or more of the example embodiments disclosed herein is improved method and apparatus for transceiving clinical trial related information. Another technical effect of one or more of the example embodiments disclosed herein is more secure client device provision for subject users. Another technical effect of one or more of the example embodiments disclosed herein is that manual steps needed for setting up client device are reduced. Another technical effect of one or more of the example embodiments disclosed herein is that more convenient overall user experience from the point of subject user is enabled. Another technical effect of one or more of the example embodiments disclosed herein is that system and service are allowed to use as complex passwords and usernames (user ID's) as seen necessary. Another technical effect of one or more of the example embodiments disclosed herein is that need to manually type username and password is removed. Another technical effect of one or more of the example embodiments disclosed herein is that need to provide username and password in other means of medium (paper, email etc.) is removed. Another technical effect of one or more of the example embodiments disclosed herein is that the need to provide or send the generated password in human readable form is eliminated. Another technical effect of one or more of the example embodiments disclosed herein is that better privacy is provided as no need to discuss with coordinators or supporting staff. For example, username would not be exposed to the coordinator user. Another technical effect of one or more of the example embodiments disclosed herein is that batch client device assignments would be easy to arrange as no need to manually assign client devices to subject users.

In an embodiment, each subject user may be identified by a subject identifier that may be verified when a subject profile is created to the system. Each subject user may be defined access rights within the system for certain parts of the information within the clinical trial records.

Advantageously, even though clinical trials are used as an example environment, different embodiments of the present disclosure can be used in various other fields. For example, embodiments can be beneficial for services relating to electronic voting, retail sales, personal face to face polls, information gathering from audience or participants, electronic restaurant menu or events ordering (new account for new customers, easy billing, analytics, etc.).

The embodiments can be utilized in the above cases in situations where a first user wants to verify that a second user is credible user and can be allowed to use the service in question. Given credentials could be optionally later assigned to other second users, for later usage.

If desired, the different functions discussed herein may be performed in a different order and/or concurrently with each other. Furthermore, if desired, one or more of the before-described functions may be optional or may be combined.

Although various aspects of the disclosed embodiments are set out in the independent claims, other aspects of the present disclosure comprise other combinations of features from the described embodiments and/or the dependent claims with the features of the independent claims, and not solely the combinations explicitly set out in the claims.

It is also noted herein that while the foregoing describes example embodiments of the present disclosure these descriptions should not be viewed in a limiting sense. Rather, there are several variations and modifications, which may be made without departing from the scope of the present disclosure as defined in the appended claims.

However, claimed embodiments do not constitute a method step for treatment of the human or animal body by surgery or therapy. No functional relationship exists between the steps related to apparatus and any therapeutic effect of the apparatus on the body.

The invention claimed is:

1. A computer implemented method for transcribing clinical trial related information between a client device operable by a plurality of users and a server apparatus, the client device and the server apparatus configured to communicate via a data network, a proprietary application of the client device comprising a client application of a clinical trial service whose server application is running on the server apparatus, wherein a coordinator user profile associated with coordinator credentials and a subject user profile associated with subject credentials are maintained by the server application at the server apparatus, the method comprising:
  receiving the coordinator credentials via a user interface by the proprietary application, accepting the coordinator credentials in response to determining the coordinator credentials being authorized credentials, and logging in the coordinator user by providing coordinator level access to the proprietary application;
  receiving, by the proprietary application, coordinator input data configured to trigger user change for the client device;
  generating and sending, in response to the coordinator input data, a request by the proprietary application to the server application indicating the triggered user change;
  receiving, by the proprietary application, subject credentials from the server application, wherein the subject credentials are associated with the subject user profile generated by the server application;
  logging out the coordinator user by disconnecting coordinator level access to the proprietary application and resetting the coordinator credentials and session data within the client device; and
  storing the subject credentials by the proprietary application for automatic first logging in of the subject user.

2. The computer implemented method of claim 1, wherein the request comprises an identifier for the subject user.

3. The computer implemented method of claim 1, further comprising:
  logging in the subject user by providing subject level access to the proprietary application using the subject credentials.

4. The computer implemented method of claim 3, further comprising:
  pre-filling, by the proprietary application, a login request template with the subject credentials.

5. The computer implemented method of claim 3, further comprising:
  automatically sending a request, by the proprietary application, to the server application to login the subject user using the subject credentials.

6. The computer implemented method of claim 3, further comprising:
  receiving subject user input data by the proprietary application; and
  sending a request, by the proprietary application, to the server application to login the subject user in response to the received user input data.

7. The computer implemented method of claim 6, wherein the subject user input data comprises at least one of the following:
   detected user input data via the user interface; and
   detected biometric data via a biometric sensor of the client device.

8. The computer implemented method of claim 3, further comprising:
   receiving activation data, by the proprietary application, from a sensing device of the client device, the sensing device comprising a positioning or a movement sensor; and
   sending a request by the proprietary application to the server application to login the subject user in response to the received activation data configured to indicate the client device being taken into use by the subject user.

9. A client device for transceiving clinical trial related information between the client device operable by a plurality of users and a server apparatus, the client device and the server apparatus configured to communicate via a data network, a proprietary application of the client device comprising a client application of a clinical trial service whose server application is running on the server apparatus, wherein a coordinator user profile associated with coordinator credentials and a subject user profile associated with subject credentials are maintained by the server application at the server apparatus, the client device comprising:
   a communication interface for transceiving information over a network;
   at least one memory including computer program code;
   the at least one memory and the computer program code configured to, with the at least one processor, cause the client device to:
   receive, by the proprietary application, the coordinator credentials via a user interface, accepting the coordinator credentials in response to determining the coordinator credentials being authorized credentials, and logging in the coordinator user by providing coordinator level access to the proprietary application;
   receive coordinator input data by the proprietary application configured to trigger user change for the client device;
   generate and send, in response to the coordinator input data, a request by the proprietary application to the server application indicating the triggered user change;
   receive, by the proprietary application, subject credentials from the server application, wherein the subject credentials are associated with the subject user profile generated by the server application;
   log out the coordinator user by disconnecting coordinator level access to the proprietary application and resetting the coordinator credentials and session data within the client device; and
   store the subject credentials by the proprietary application for automatic first logging in of the subject user.

10. The client device of claim 9, wherein the at least one memory and the computer program code are further configured to, with the at least one processor, cause the client device to contain an identifier for the subject user in the request.

11. The client device of claim 9, wherein the at least one memory and the computer program code are further configured to, with the at least one processor, cause the client device to log in the subject user by providing subject level access to the proprietary application using the subject credentials.

12. The client device of claim 11, wherein the at least one memory and the computer program code are further configured to, with the at least one processor, cause the client device to pre-fill, by the proprietary application, a login request template with the subject credentials.

13. The client device of claim 11, wherein the at least one memory and the computer program code are further configured to, with the at least one processor, cause the client device to automatically send a request, by the proprietary application, to the server application to login the subject user using the subject credentials.

14. The client device of claim 11, wherein the at least one memory and the computer program code are further configured to, with the at least one processor, cause the client device to:
   receive subject user input data by the proprietary application; and
   send a request, by the proprietary application, to the server application to login the subject user in response to the received user input data.

15. The client device of claim 14, wherein the subject user input data comprises at least one of the following:
   detected user input data via the user interface; and
   detected biometric data via a biometric sensor of the client device.

16. The client device of claim 11, wherein:
   the client device comprises a sensing device that comprises a positioning sensor or a movement sensor; and
   the at least one memory and the computer program code are further configured to, with the at least one processor, cause the client device to:
   receive activation data, by the proprietary application, from a sensing device of the client device; and
   send a request by the proprietary application to the server application to login the subject user in response to the received activation data configured to indicate the client device being taken into use by the subject user.

17. A non-transitory computer readable storage medium for transceiving clinical trial related information between a client device operable by a plurality of users and a server apparatus, the client device and the server apparatus configured to communicate via a data network, a proprietary application of the client device comprising a client application of a clinical trial service whose server application is running on the server apparatus, wherein a coordinator user profile associated with coordinator credentials and a subject user profile associated with subject credentials are maintained by the server application at the server apparatus, the non-transitory computer readable storage medium comprising computer executable program code, which when executed by at least one processor of the client device, causes the client device to:
   receive the coordinator credentials via a user interface by the proprietary application, accepting the coordinator credentials in response to determining the coordinator credentials being authorized credentials, and logging in the coordinator user by providing coordinator level access to the proprietary application;
   receive, by the proprietary application, coordinator input data configured to trigger user change for the client device;
   generate and send, in response to the coordinator input data, a request by the proprietary application to the server application indicating the triggered user change;
   receive, by the proprietary application, subject credentials from the server application, wherein the subject credentials are associated with the subject user profile generated by the server application;

log out the coordinator user by disconnecting coordinator level access to the proprietary application and resetting the coordinator credentials and session data within the client device; and store the subject credentials by the proprietary application for automatic first logging in of the subject matter.

\* \* \* \* \*